US00PP17666P2

(12) United States Plant Patent
Van Opstal

(10) Patent No.: US PP17,666 P2
(45) Date of Patent: Apr. 24, 2007

(54) ***LEUCOTHOE* PLANT NAMED 'CURLY RED'**

(50) Latin Name: *Leucothoe axillaris*
Varietal Denomination: CURLY RED

(76) Inventor: Ron Van Opstal, St. Willebrordusstraat 3, 4882 NM Zundert (NL)

( * ) Notice: Subject to any disclaimer, the term of this patent is extended or adjusted under 35 U.S.C. 154(b) by 138 days.

(21) Appl. No.: 11/053,243

(22) Filed: Feb. 7, 2005

(51) Int. Cl.
*A01H 5/00* (2006.01)

(52) U.S. Cl. ..... Plt./373
(58) Field of Classification Search ..... Plt./373, Plt./226
See application file for complete search history.

(56) References Cited

PUBLICATIONS

GTITM UPOV Citation for 'Curly Red' as per QZ PBR 20011519, Sep. 23, 2002.*
GTITM UPOV Citation for 'Curly Red' as per NL PBR LCT0002, Sep. 21, 2001.*

* cited by examiner

*Primary Examiner*—Anne Marie Grunberg
*Assistant Examiner*—Louanne Krawczewicz Myers

(57) ABSTRACT

A new cultivar of *Leucothoe* named 'CURLY RED' that is characterized by curled growth of the foliage which in its spring season of new growth exhibits burgundy red coloration which turns purple in summer and turns dark green as the plant matures. This trait sets 'CURLY RED' apart from all other existing varieties of *Leucothoe* known to the inventor.

2 Drawing Sheets

Genus: *LEUCOTHOE.*
Species: *axillaris.*
Denomination: 'CURLY RED'.

BACKGROUND OF THE INVENTION

The present invention relates to a new and distinct cultivar of *Leucothoe* that is grown for use as an ornamental plant in the landscape and as a decorative indoor foliage plant. The new cultivar is known botanically as *Leucothoe axillaris* and will be referred to hereinafter by the cultivar name 'CURLY RED'. In 1996, the inventor, a commercial grower of acid-loving plants including *Gaultheria, Pieris* and *Leucothoe* observed in his crop of *Leucothoe axillaris* variety 'Zeblid' (unpatented, also sold under the trade name Scarletta) a single plant which exhibited highly unusual curling and reddening of the foliage, particularly the new foliage growth. The inventor removed and isolated this naturally occurring whole plant mutation, not knowing whether the curling of the leaves was the result of a pathogenic problem or a spontaneous and permanent genetic mutation.

The inventor observed that as the single isolated plant continued to grow, its characteristics remained stable—that is, the foliage of the growing plant retained the characteristic curling and purple-red coloration as herein described. The inventor carried out the first asexual propagation of 'Curly Red' in the summer of 2001, in Boskoop, The Netherlands by taking stem cuttings from the current year's shoot growth. The resulting plants were compared with the original plant discovered. All plants resulting from the first and subsequent cycles of asexual propagation have remained stable and have been determined by the inventor to reproduce true to the 'Curly Red' type, with no "reversion" to the characteristic leaf type of all cultivars of the species *LEUCOTHOE axillaris* known to the inventor, including 'Zeblid', none of whose leaves curl at all. However, the new spring growth of the foliage of all cultivars of *LEUCOTHOE*

*axillaris* does tend to emerge with a reddish-brown coloration.

When compared with the parental cultivar 'Zeblid', 'CURLY RED' is observed to have an identical form and characteristics, with the exception that the new spring growth of 'CURLY RED' emerges and remains noticeably curled, whereas the foliage of 'Zeblid' emerges and remains flattened as is typical of other known cultivars of the species *LEUCOTHOE axillaris.* The color of the curled leaves of 'CURLY RED' tends towards purple-red whereas the color of the emerging leaves of 'Zeblid' tends towards reddish-brown.

The inventor filed an application for European Community Plant Variety Rights for 'CURLY RED' on Nov. 5, 2001, application serial number 20011519, and subsequently granted on Sep. 23, 2002, grant number 10129. The inventor also filed in The Netherlands an application for Netherlands Plant Breeders Rights, application number PBR LCT002, which was published on Sep. 21, 2001.

'CURLY RED' was first shown to the public as specimen plants in the inventor's booth at the Plantarium Nursery Show in Boskoop, The Netherlands, in August 2003. The inventor retained control and possession of all of his plants of 'CURLY RED' until the first sale and delivery which took place in August 2004. 'Curly Red' shared with three other plant varieties, the award of "most striking plant novelty" at the Aalsmeer Flower Market in November 2004.

SUMMARY OF THE INVENTION

The distinguishing characteristic of the new *Leucothoe* cultivar 'CURLY RED' is the curled growth of the foliage which in its spring season of new growth exhibits burgundy red coloration which turns purple in summer and turns dark green as the plant matures. This trait sets 'CURLY RED' apart from all other existing varieties of *Leucothoe* known to the inventor.

BRIEF DESCRIPTION OF THE DRAWINGS

The accompanying color drawing illustrates the overall appearance of the new *Leucothoe* variety 'CURLY RED' showing the colors as true as it is reasonably possible to obtain in colored reproductions of this type. Colors in the drawings may differ from the color values cited in the detailed botanical description, which accurately describes the actual colors of the new variety 'CURLY RED'.

The drawing labeled as FIG. 1 illustrates a whole plant which is approximately twenty seven months old from a cutting. The cutting was rooted in a frost-protected greenhouse in spring 2002, potted in a 1.5 liter container in late 2002 and allowed to grow for a further 18 months without pinching. The drawing depicts the growth in summer, after the new season's red coloration has begun to change to purple and then later in the year, to very dark green. The entire growth cycle took place at the Inventor's nursery in Zundert, The Netherlands.

Figure 1:
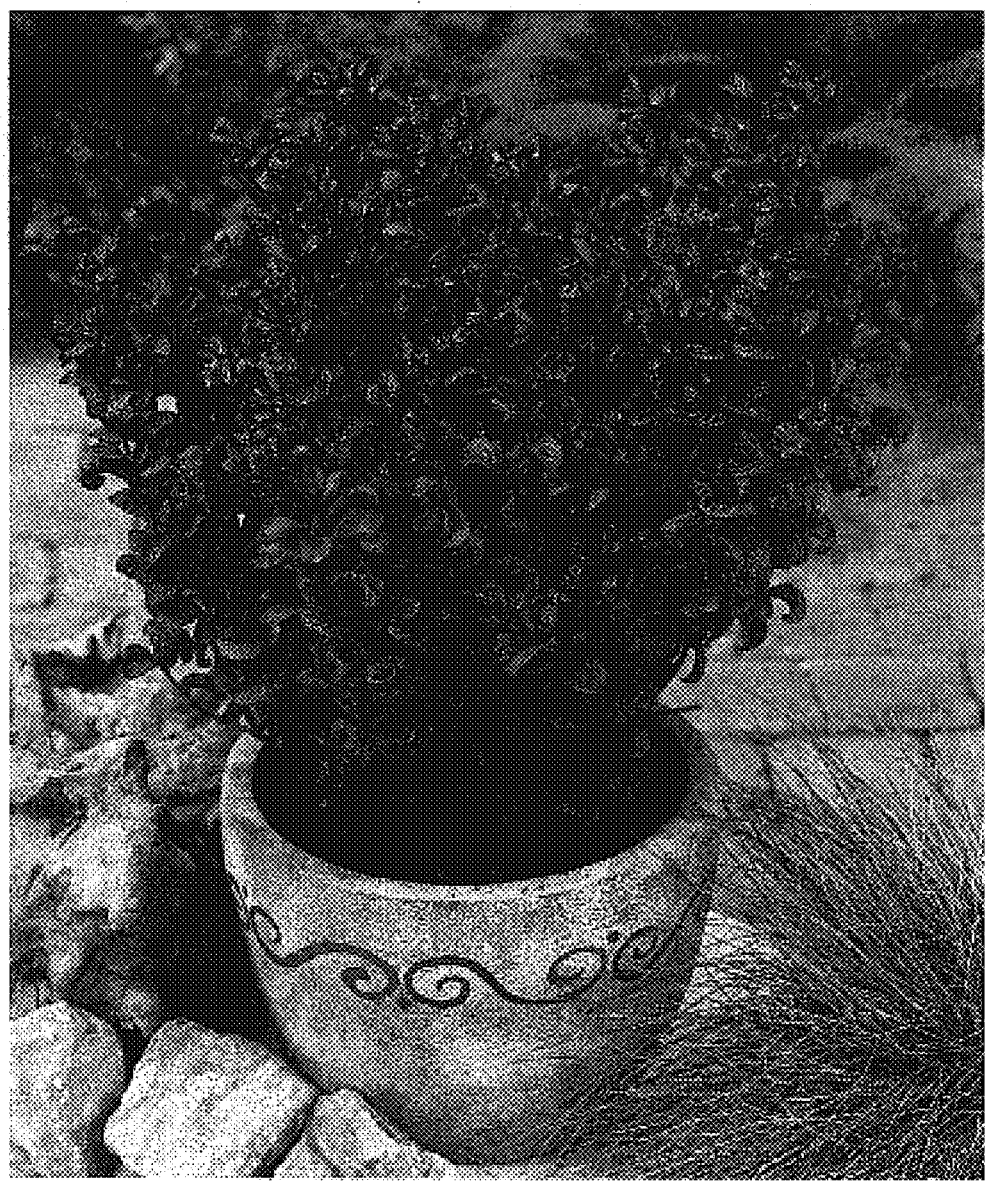
Figure 2:
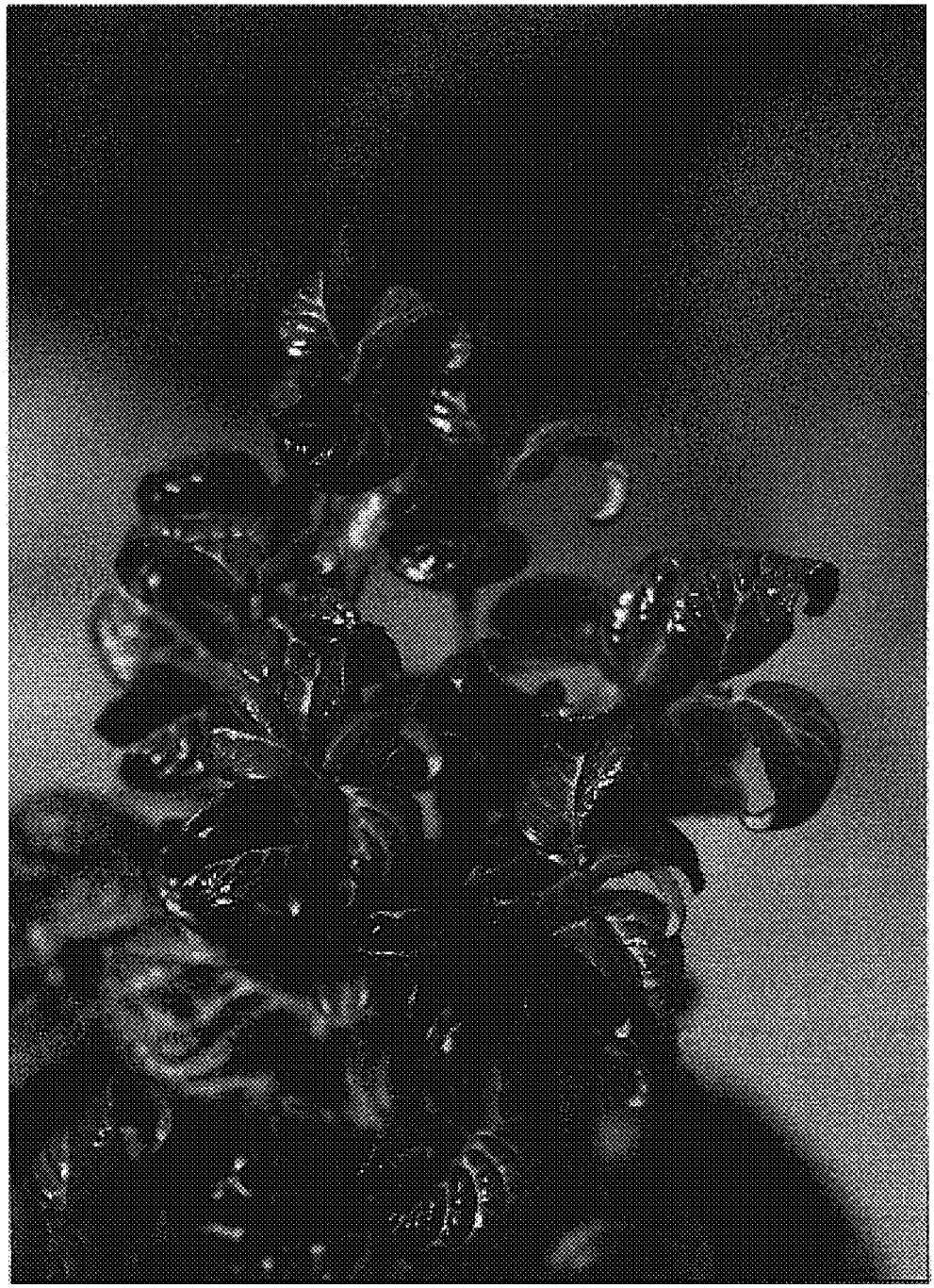

The drawing labeled as FIG. 2 illustrates a close-up view of the characteristic curled and reddened new foliage growth which appears in spring. The drawings were made using conventional techniques and although foliage colors may appear different from actual colors due to light reflectance, they are as accurate as possible by conventional photography.

BOTANICAL DESCRIPTION OF THE PLANT

The following is a detailed description of the *Leucothoe* cultivar named 'CURLY RED'.

Data was collected in Zundert, The Netherlands from a two years old plant which had been grown as follows: A cutting of 'CURLY RED' was rooted in a frost-protected greenhouse in spring 2002, potted in a 1-liter container in late 2002 and allowed to grow for a further 18 months without pinching.

Color determinations are in accordance with the 2001 Edition of The Royal Horticultural Society Colour Chart except where general color terms of ordinary dictionary significance are used.

Botanical classification:
- *Genus.*—*Leucothoe.*
- *Species.*—*axillaris.*

Denomination 'Curly Red'.

Use: Ornamental.

Parentage: 'CURLY RED' is a naturally occurring whole plant mutation of the variety of *Leucothoe axillaris* known as 'Zeblid'.

Type: Evergreen shrub.

Vigor: Low vigor, approximately 10 cm–12 cm new growth per season.

Habit: Upright.

Plant shape: Flattened globular.

Height (at maturity): 40 cm. in height.

Width (at maturity): 45 cm. in width.

Hardiness: USDA Zone 7.

Propagation: Propagation is most effectively carried out by taking firm tip cuttings in summer from the current year's shoot growth. Under these conditions, no rooting chemical or hormone is believed to be necessary or beneficial.

Root system: Very fine.

Soil: Moist acidic soil, ideally with pH value between 4.2 and 5.0

Sunlight: Full sun to semi-shade.

Time to initiate rooting: Slow: Approximately 8 weeks are needed to produce roots on an initial cutting.

Temperature to initiate rooting: 20° to 25° Centigrade substrate temperature.

Crop time: 24 months are needed to produce a finished 1.5 liter container from a rooted cutting.

Disease and pests: No specific susceptibility or resistance has been observed.

Stem:
- *Stem diameter.*—5 mm.
- *Stem length.*—40 cm.
- *Stem shape.*—Rounded.
- *Surface.*—Smooth, dull.
- *Strength.*—Strong.
- *Pubescence.*—None.
- *Lenticels.*—None.
- *Stem color.*—138B.
- *Basal branching.*—None.
- *Lateral branch dimensions.*—25 cm in length, 3 mm in diameter.
- *Internode length.*—1.0 cm–1.5 cm between nodes.
- *Lateral branching.*—Naturally occurring: approximately 50 lateral branches without pinching.

Foliage:
- *Type.*—Evergreen.
- *Leaf arrangement.*—Alternate.
- *Leaf division.*—Simple.
- *Number of leaves per lateral branch.*—Approximately 25.
- *Leaf attachment.*—Petiolate.
- *Leaf dimensions.*—2.9 cm in length and 2.5 cm. in width.
- *Leaf shape.*—Ovate.
- *Leaf curling.*—Tip strongly curved downwards, tip occasionally recurves to touch leaf underside. Curled tips cannot be uncurled without breaking.
- *Leaf base.*—Shallowly cordate.
- *Leaf apex.*—Acute.
- *Leaf venation.*—Pinnate.
- *Leaf margin.*—Serrate.
- *Leaf color* (*spring growth at most intense red stage, adaxial surface*).—46A, midrib and veins 161C.
- *Leaf color* (*spring growth at most intense red stage, abaxial surface*).—46A where surface unbroken; tends to 46D towards tip and if surface broken.
- *Leaf color* (*summer growth at most intense purple stage, both surfaces*).—59B and 59C.
- *Leaf color* (*mature leaf, adaxial surface*).—Very dark green; between 139A and N189A but much darker.
- *Leaf color* (*mature leaf abaxial surface*).—138B.
- *Midrib and veins.*—Prominent on adaxial (convex) surface; absent on abaxial surface. Vein color (spring, summer): 161C. Vein color (mature): 143C.
- *Leaf surface* (*both surfaces*).—Strongly bullate, thick, leathery, glossy except in spring when abaxial surface of recurved tip may be broken, rough.
- *Petiole dimensions.*—Up to 3 mm in length, 1.8 mm in diameter.
- *Petiole color.*—143C.
- *Petiole surface.*—Smooth.

Flowers: Although vestigial flowers may be present in apex, none have been observed.

Reproductive organs: Not observed.

Seed: None observed.

What is claimed is:

1. A new and distinct variety of *Leucothoe* plant named 'CURLY RED' as described and illustrated.

* * * * *